United States Patent [19]

Koike

[11] Patent Number: 5,561,052
[45] Date of Patent: Oct. 1, 1996

[54] PROCESS FOR DETECTING OXIDIZED LIPIDS AND PROCESS FOR FORMING OXIDIZED LIPIDS

[76] Inventor: Katsumasa Koike, 9-12 Kawada-cho, Shinjuku-ku, Tokyo 162, Japan

[21] Appl. No.: 446,082

[22] Filed: May 19, 1995

Related U.S. Application Data

[63] Continuation-in-part of Ser. No. 77,076, Jun. 16, 1993, abandoned.

[30] Foreign Application Priority Data

Jun. 18, 1992 [JP] Japan .................................. 4-200082
May 12, 1993 [JP] Japan .................................. 5-144170

[51] Int. Cl.$^6$ ............................. C12Q 1/26; G01N 33/00
[52] U.S. Cl. .......................... 435/25; 435/35; 435/134; 435/968; 436/13; 436/57; 436/59; 436/60; 436/71; 436/81; 436/82; 436/173; 436/174
[58] Field of Search ............................... 435/25, 35, 134, 435/968; 436/13, 57, 59, 60, 71, 81, 82, 173, 174

[56] References Cited

FOREIGN PATENT DOCUMENTS

| | | |
|---|---|---|
| 0141343 | 5/1985 | European Pat. Off. . |
| 3809171 | 9/1988 | Germany . |
| 93/03450 | 2/1993 | WIPO . |

OTHER PUBLICATIONS

Van Os et al, *Biochim Biophys Acta*, vol. 574, No. 1, pp. 103–111, 1979.
Laignelet et al, *Biological Abstracts*, vol. 79, Ref. #49013, 1985 (Cebensm–Wiss Technol 17(4):226–230, 1984).
Striegel, *Dissertation Abstracts*, vol. 53, No. 4C, p. 733, 1989.
Maguire et al, *Biochim. Biophys. Res. Commun.*, vol. 188, No. 1, pp. 190–197, Oct. 15, 1992.
Berman et al, *Br. J. Pharmacol.*, vol. 108, No. 4, pp. 920–926, 1993.
Gutteridge, J. M. C., et al., "The measurement and mechanism of lipid peroxidation in biological systems", 1990, pp. 129–135, Elsevier Science Publishers Ltd (UK).
Chemical Abstracts, vol. 112, No. 19, 7 May 1990, abstract No. 175109a.
Database WPI, Section Ch, Week 8520, Derwent Publications, Class E12, AN 85-118817 & JP 60 058 538, 4 Apr. 1985, abstract.
Yamauchi, R., et al., Agric. Biol. Chem. (1988), vol. 52, pp. 849–850.
Chemical Abstracts, vol. 115, No. 17, 28 Oct. 1991, abstract No. 178256u.
Chemical Abstracts, vol. 109, No. 25, 19 Dec. 1988, abstract No. 225930x.
Cramer, G. L., et al., Analytical Biochemistry (1991), vol. 193, pp. 204–211.

*Primary Examiner*—Elizabeth C. Weimar
*Assistant Examiner*—Abdel A. Mohamed
*Attorney, Agent, or Firm*—Beveridge, DeGrandi, Weilacher & Young, L.L.P.

[57] ABSTRACT

There are disclosed a process for detecting and determining an oxidized lipid in a specimen, which is capable of readily and accurately determining a specimen as containing an oxidized lipid, and a process for forming a water-soluble oxidized lipid having a hydroperoxide group which has specific influence on a living body. A specimen is detected and determined to contain an oxidized lipid by adding a lanthanide shift reagent to a specimen, followed by spectroscopic analysis thereof. An oxidized lipid is formed by adding superoxide dismutase (SOD) and $CuSO_4$ to (1) an emulsion prepared by dissolving linoleic acid or arachidonic acid in deuterated methyl alcohol and adding the solution to a deuterated phosphate buffer under stirring, or to (2) a low density lipoprotein solution sufficiently dialyzed against an undeuterated phosphate buffer; followed by irradiation with long-wave ultraviolet light.

25 Claims, 11 Drawing Sheets

PROCESS FOR DETECTING OXIDIZED LIPIDS AND PROCESS FOR FORMING OXIDIZED LIPIDS

REFERENCE TO A RELATED APPLICATION

This is a continuation-in-part of my application Ser. No. 08/077,076 filed Jun. 16, 1993, now abandoned and which is relied on and incorporated herein by reference in its entirety.

BACKGROUND OF THE INVENTION

The present invention relates to a process for detecting a water-soluble oxidized lipid. The process is capable of readily confirming that a specimen contains a water-soluble oxidized lipid. The present invention also concerns a process for forming a water-soluble lipid.

Oxidized lipids are believed to cause adverse effects in vivo, and have been pointed out to be responsible for arteriosclerosis, cancer, inflammation, aging, and other conditions. It is also believed that low density lipoproteins which account for a majority of lipids in blood are related to the above-mentioned disorders.

On the other hand, oxidized lipids which are controlled and produced by enzymes in vivo, such as prostaglandin and leukotriene, are likely to become substances having a strong influence on a living body.

Various methods for detecting a stable oxidized lipid or a final metabolite thereof have been developed; however, none of these methods permits satisfactory evaluation of the lipid oxidation process, this is partially due to difficulty in non-destructively isolating and differentiating specific oxidized lipids from other substances present in a sample that interfere With assays. These methods include, for example, the following: an iodine oxidation method which involves ionizing iodine by oxidation, followed by emission spectroscopic analysis on the ionized iodine; TBARS (thiobarbituric acid reactive substance) measuring method which involves producing a pigment by reaction with malondialdehyde as a peroxide lipid metabolite, followed by determination of the pigment by means of an absorption spectrophotometer or a fluorophtometer; conjugated diene determination method which involves determining a conjugated diene based on the fact that a conjugated diene is formed by peroxidation of an unsaturated fatty acid; high performance liquid chromatography (HPLC) method which involves separating and determining a peroxide lipid sample by means of a high performance liquid chromatograph; and gas chromatography method which involves esterifying a peroxide lipid sample, followed by separation and determination by means of gas chromatography.

However, the iodine oxidation method and the conjugated diene determination method which determine an oxidized lipid have a drawback in that they are not suitable for analysis of a sample containing an impurity. Furthermore, the iodine oxidation method, the TBARS method, and the conjugated diene determination method are non-specific determination methods, i.e., these methods do not directly determine an oxidized lipid per se, but indirectly determine an oxidized lipid by determining a by-product which is formed through formation or decomposition of an oxidized lipid.

On the other hand, the HPLC method and the gas chromatography method are specific methods which directly determine an oxidized lipid per se. In the HPLC method, however, it takes a long period of time to complete determination, so that a sample can undergo denaturation. In addition, an oxidized lipid per se is likely to undergo alteration by a solvent such as ethyl ether or ethanol. Furthermore, in the gas chromatography method, a sample is likely to undergo alteration through esterification treatment or the like.

Various methods for producing an oxidized lipid have heretofore been reported. Among these methods, there may be mentioned, for example, the following: a method which involves adding a transition metal such as copper cation ($Cu^+$) or iron cation ($Fe^{2+}$) to a lipid sample, and allowing the mixture to stand at a temperature of about 37° C. for a period of 20 to 30 hours; a method which involves irradiating a sample, that is preliminarily added with a photosensitive substance, with light; and a method which comprises oxidation by an enzyme such as lipoxygenase or cyclooxygenase.

As described above, there has never been disclosed a method for precisely detecting and analyzing an oxidized lipid having physiological influence or an unstable oxidized lipid which adversely affects a body. In addition, there has not yet been developed a method for forming a water-soluble oxidized lipid having a hydroperoxide group which has specific influence on a living body. Furthermore, a method for precisely detecting a water-soluble oxidized lipid having a hydroperoxide group has not been developed. Accordingly, it has been impossible to evaluate formation of a specific water-soluble oxidized lipid. Water-soluble oxidized lipids having a hydroperoxide group have potentiality to be used as pharmaceuticals or intermediates thereof. For example, the water-soluble oxidized lipid can be used as an anticarcinogen when it comes into contact (e.g., via injection) with cancer cells since such oxidized lipids damage cells when provided with free radicals. The oxidized lipids can also be applied as a vasodilator for treatment of arterial infractions such as encephalic and myocardial infractions.

An object of the present invention was to solve the above-mentioned problems.

SUMMARY OF THE INVENTION

One object of the present invention to provide a process for detecting an oxidized lipid which is capable of readily and precisely determining a specimen as containing an oxidized lipid.

It is another object of the present invention to provide a process for forming a water-soluble oxidized lipid having a hydroperoxide group which has specific influence on a living body.

It is still another object of the present invention to provide a process which is capable of directly detecting an oxidized lipid in a biological sample such as plasma.

To attain the above-mentioned and other objects, the present invention detects an oxidized lipid in a specimen by adding a lanthanide shift reagent to a specimen and subjecting the resultant mixture to spectroscopy. For example, as the specimen, free fatty acids such as linoleic acid or arachidonic acid which is oxidized by soybean lipoxygenase may be used.

As the lanthanide shift reagent, for example, dysprosium cation may be used.

As a process for forming a water-soluble oxidized lipid containing hydroperoxide group, superoxide dismutase (SOD) and $CuSO_4$ are added to (1) an emulsion prepared by linoleic acid or arachidonic acid in deuterated methyl alcohol and adding the solution to a deuterated phosphate buffer under stirring, or to (2) a dissolved low density lipoprotein solution sufficiently dialyzed against undeuterated phosphate buffer, and irradiation with a long-wave ultraviolet light.

Furthermore, an oxidized lipid is detected in a specimen is detected by:

adding superoxide dismutase (SOD) and $CuSO_4$ to (1) an emulsion prepared by dissolving linoleic acid or arachidonic acid in deuterated methyl alcohol and adding the solution to a deuterated phosphate buffer under stirring, or to (2) a low density lipoprotein solution sufficiently dialyzed against an undeuterated phosphate buffer;

conducting irradiation with a long-wave ultraviolet light to form an oxidized lipid;

adding dysprosium tripolyphosphate anion to the oxidized lipid; and subjecting the mixture to proton NMR spectroscopy by means of a nuclear magnetic resonance spectrometer.

BRIEF DESCRIPTION OF THE DRAWINGS

The present invention will be further understood with reference to the drawings, wherein.

DETAILED DESCRIPTION OF THE INVENTION

Figure 1:
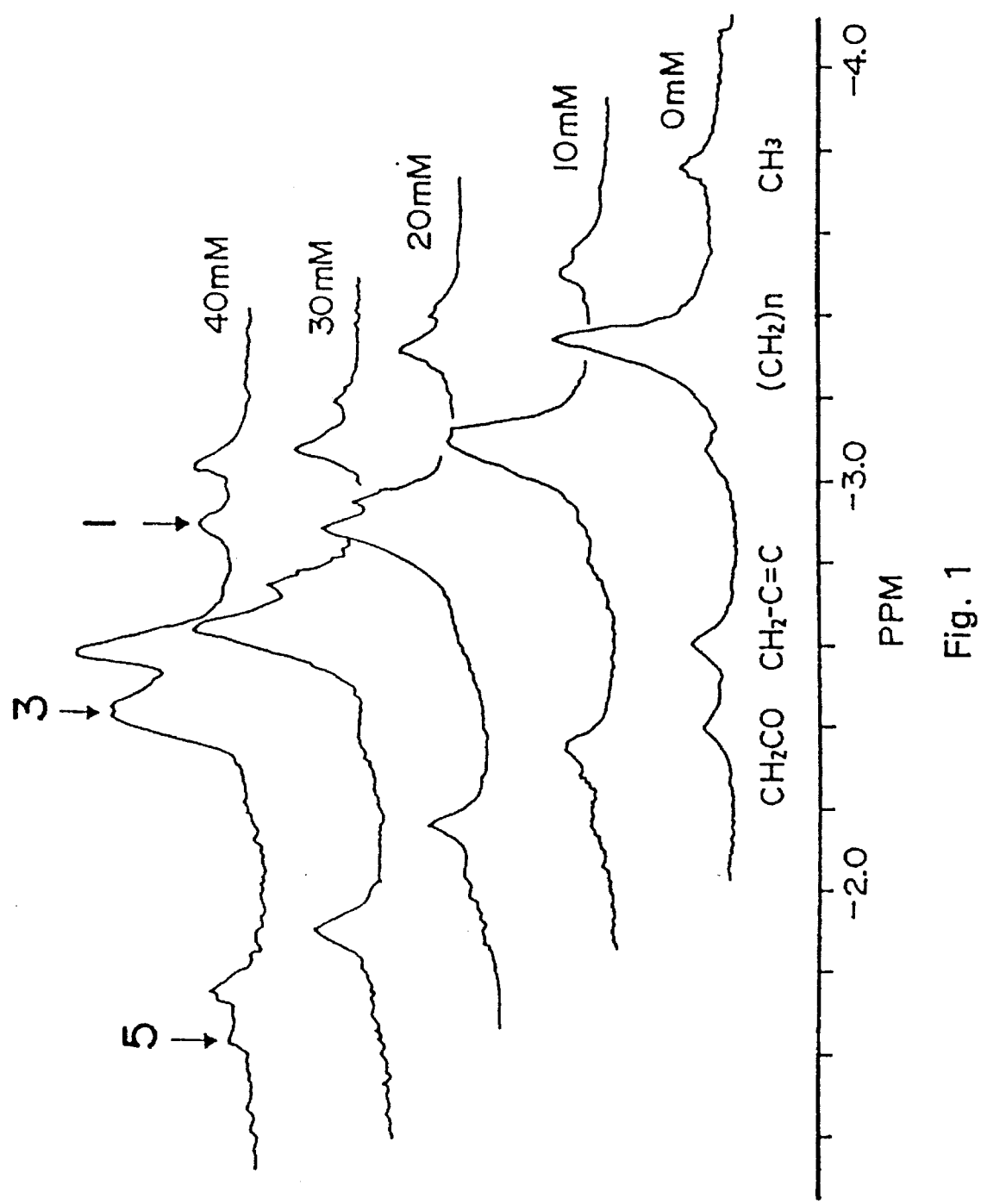
FIG. 1 is a graph showing the influence of dysprosium (Dy) concentration upon proton signals of an oxidized lipid.

In one aspect, the present invention is directed to confirm the presence of an oxidized lipid in a specimen by adding a lanthanide shift reagent to a specimen, followed by subjecting the mixture to spectroscopy. This is based on the fact that when a lanthanide shift reagent is added to a specimen, difference in proton signals is observed between the case where the substance is an oxidized lipid and the case where the substance is not an oxidized lipid. Accordingly, by detecting the difference through spectroscopy, the oxidized lipid is detected in the specimen.

Furthermore, the present invention is also directed to the formation of a water-soluble oxidized lipid having a hydroperoxide group which has considerable influence on a living body by the use of a low density lipoprotein or fatty acid.

According to the present invention, an oxidized lipid is detected in a specimen by adding a lanthanide shift reagent to the specimen, followed by subjecting the mixture to spectroscopy. As the specimen, use can be made, for example, of linoleic acid or arachidonic acid which is each oxidized by soybean lipoxygenase (other lipoxygenases can also be utilized, lipoxygenases are found not only in soybeans but also in potatoes, humans, pigs, and rabbits; these lipoxygenases include 5-lipoxygenase (potato), 12-lipoxygenase (human, porcine), and 15-lipoxygenase (human, rabbit)). As an example of the lanthanide shift reagent, dysprosium tripolyphosphate anion is used.

In this connection, there may be used as the lanthanide shift reagent europium cation ($Eu^{3+}$) and thulium cation ($Tm^{3+}$) as well as dysprosium cation. The use of europium cation or thulium cation enables substantially the same result as in the case of dysprosium cation to be obtained. As the chelating agent, ethylenediaminetetraacetic acid and the like may be used as well as the tripolyphosphate.

For example, $^{13}$C-NMR spectroscopy analysis provides significant information on the oxidized lipid just as $^1$H-NMR analysis, using the lanthanide shift reagents.

The water-soluble oxidized lipid having a hydroperoxide group which has specific influence on a living body is very unstable. This is because the water-soluble oxidized lipid having a hydroperoxide group is more susceptible to conversion at its hydroperoxide group at higher pH levels, especially at a pH level of about 7.2 or higher which includes an optimal pH level of soybean lipoxygenase activity. Therefore, even if the water-soluble oxidized lipid having a hydroperoxide group is formed in a large amount by the activity of soybean lipoxygenase, almost all of it is therefor converted in a very short period of time (at most several seconds) in a reaction system having, for example, a pH of 9.0. To obtain the water-soluble oxidized lipid having a hydroperoxide group according to the present invention in a satisfactory amount, it is preferred to add a chelating agent (e.g., EDTA) to the stocking material after reaction or to maintain the stocking environment under strong acidic conditions, thereby preventing the hydroperoxide group of the water-soluble oxidized lipid from otherwise instantly undergoing conversion. The water-soluble oxidized lipids formed by the process of the present invention are present in the form of free fatty acids (not bound fatty acids).

Heavy hydrogen exists in nature in the form of a hydrogen atom to which a neutron is added and the weight of which is 2. There is no difference between chemical reactions made in a solution of heavy water ($D_2O$ or $^2H_2O$) as specified herein and those made in a solution of light water ($^1H_2O$). The deuterated solution disclosed herein includes a certain amount of heavy hydrogen ($^1H$ proton). On the other hand, a normal solution naturally include very small amounts of heavy hydrogen ($^2H$, 0.0015% of which is included in natural hydrogen). Thus, deuteration does not produce differences in chemical reactions except for nuclear physical reactions. More particularly, "pure water" as a chemical term means water which does not include any impurity. However, pure water consists of 99,985 $^1H_2O$ and 0,015 $^2H_2O$. Therefore, in the chemical field, a pure substance is recognized to be pure and has no impurity, even though it includes heavy hydrogen. In other words, in the chemical field, there is no difference between heavy water and light water. The contents of heavy water differ based on the locations from which water samples are taken for experiments. However, the differences in the content of heavy water is not a problem in the organic chemistry field to which the subject matter of this application belongs. Deuteration is not necessary for producing oxidized lipids.

Deuteration herein is carried out because the water proton signal overlaps the lipid proton signal due to the huge amount of water proton signal of water, which shares the most part of the test solution in ordinary chemical procedures, produced in the case of spectral analysis of proton signal contained in the lipid by means of proton NMR. To reduce the influence, heavy hydrogen ($^2H$ or D) is used because the resonant frequency of the heavy hydrogen is quite different from that of the proton signal in the lipid and the characteristics of chemical reaction is the same as that of proton($^1H$).

It is considered that there is no difference as to chemical reactions (i.e., production of oxidized lipids) between the experiments wherein hydrogen (proton) is used and those wherein heavy hydrogen is used, and those experiments are considered as the same. It is well understood and common knowledge that deuteration is used in many other proton NMR experiments.

It is possible by the simple combination of the shift reagent and NMR spectrometry to evaluate the degree of oxidation of a lipid in a living body or a lipid used in a food or other industrial products.

In exchange for linoleic acid and arachidonic acid as utilized herein, various other substrates (e.g., free fatty acids) can be utilized for the production of the corresponding oxidized lipids that lead to pharmaceutical products. These substances include, for instance, alpha-linolenic acid, gamma-linolenic acid, eicosapentaenoic acid (EPA), eicosatrienoic acid, eicosadienoic acid, docosahexaenoic acid, docosapentaenoic acid, and docosatetraenoic acid. All polyunsaturated fatty acids having 1.4-cis,cis-pentadiene structure are basically oxidized by the method described herein. These acids, as physiologically stimulating substances, can be direct components of pharmaceutical products or can be transformed into applicable substances by applying various chemical processes.

Method for Oxidation of Linoleic Acid and Arachidonic Acid with Soybean Lipoxygenase Linoleic acid and arachidonic acid (from Sigma Chemical Co.) can be used as substances to be examined and are prepared in the following manner:

First, linoleic acid and arachidonic acid are separately dissolved into deuterated methyl alcohol (Methyl-$d_3$ alcohol-d: $CD_3OD$, from Sigma Chemical Co.) at a concentration of 0.1M. The solutions are each emulsified in a 20 mM oxygen-saturated deuterated phosphate buffer (pH 7.0) to prepare a 4 mM linoleic acid emulsion and a 2 mM arachidonic acid emulsion. Then the emulsions were divided into two parts: those containing no superoxide dismutase (SOD) and those added with superoxide dismutase (SOD) at a concentration of 0.1 U/ml. For oxidation of the fatty acids, soybean lipoxygenase is added to each of the emulsions at a final concentration of 2000 U/ml. The final volume is adjusted to 1 ml and oxidation is conducted at a temperature of 0° C.

After an elapse of a predetermined period of time, soybean lipoxygenase is inactivated by acidifying the reaction solution to pH 4 with 0.1M deuterium chloride. The purpose of adding 0.1M deuterium chloride is to prevent the reaction of soybean lipoxygenase by making it acidic; making it acidic, in the range of pH 4.0, has the additional benefit of stabilizing the hydroperoxide group of the oxidized lipid. Then ethylenediaminetetraacetic acid (EDTA) is added to the solution at a concentration of 1 mM and the solution is adjusted to pH 7.0 with 0.1M NaOH dissolved in deuterium oxide and the volume of the solution is finally adjusted to 1.5 ml with 20 mM deuterated phosphate buffer; this process of adding EDTA is necessary because a hydroperoxide group would be destroyed instantaneously in a pH 7.0 phosphate deuteride buffer (the solution has to be at pH 7.0 because the Dy(PPP) reagent's pH is 7.4, if the solution were acidic then deposition of the reagent occurs and the sample becomes useless for NMR measurement).

To the oxidized lipid samples, glutathione is added at various concentrations (0, 1, 5, and 50 nM) and glutathione peroxidase at a concentration of 0.2 U/ml, thereby adjusting the final volume to 1.5 ml. Reaction is advanced at 30° C. for 10 min. Thereafter, to each of the samples is added dysprosium tripolyphosphate anion as a lanthanide shift reagent at a concentration of 40 mM.

In the process for forming dysprosium tripolyphosphate anion (Dy(PPP)) solution, 200 mM dysprosium chloride ($DyCl_3$, Aldrich Chemical Co.) and 480 mM pentasodium tripolyphosphate are thoroughly stirred in deuterium oxide; reagents which are purer than commercial products are advantageous. The solution, though it has a sediment, is adjusted to pH 7.4 with deuterium chloride, thereby some of the precipitate will be dissolved. Then the solution is centrifuged at 3000 g for 30 min to remove the remaining sediment. This solution is used as 200 mM dysprosium tripolyphosphate anion ($Dy(ppp)_2^{-7}$) solution which are to be added to the specimen.

Determination of Oxidized Lipid by $^1H$-NMR Spectroscopy

According to the present invention, an oxidized lipid is detected in a specimen by adding the 200 mM dysprosium tripolyphosphate anion solution as a lanthanide shift reagent to the specimen, followed by spectroscopy of the mixture. For the spectroscopy, hydrogen nucleus (proton) NMR analysis ($^1H$-NMR spectroscopy) by means of a 360MHz-nuclear magnetic resonance spectrometer equipped with a computerized analyzer is used; preferably, the main magnetism ($H_o$) strength of NMR is at least 240MHz or more (NMR resolution is reduced substantially when shift reagents are added, thus causing the width of proton peaks to broaden and overlap each other; therefore, low-resolution NMR would make subject peak identification difficult).

Proton spectra are obtained at a probe temperature of 35° C. and the spectra are accumulated by repeating Free Induction Decay (FID) 512 times. H$_2$O peak is presaturated by 4 sec. of 200 mW of gated, continuous-wave, single-frequency radio wave irradiation. Parameters of the spectra are 8192 data points, a spectral width of 7246 Hz, and acquisition time of 0.565 sec. The spinning rate of the sample tube is 15 Hz and the frequency was deuterium-locked prior to determination.

Influence of Dysprosium Cation (Dy$^{3+}$) Concentration On Proton Signal of Oxidized Lipid According to the present invention, a water-soluble oxidized lipid is detected in a specimen in view of the fact that when dysprosium cation (Dy$^{3+}$) is added to oxidized lipid samples at various concentrations, a difference in proton signals is observed between the case where the sample is a water-soluble oxidized lipid and the case where the sample is not a water-soluble oxidized lipid.

Accordingly, the influence of dysprosium cation (Dy$^{3+}$) cation concentrations on proton signal of oxidized lipid is observed by adding dysprosium tripolyphosphate anion (Dy(ppp)$_2^{-7}$) to oxidized lipid samples at various concentrations (see FIG. 1). The values in FIG. 1 show concentrations (mM) of dysprosium cation (Dy$^{3+}$) added to the samples. CH$_3$, (CH$_2$)$_n$, CH$_2$—C=C., and CH$_2$CO in FIG. 1 show proton signals in the fatty acid molecule which have already been identified, i.e., proton signals at the above-mentioned sites in the fatty acid.

The scale of the shift is based on H$_2$O peak as the reference point (0 PPM). Peak 1 is a peak separated from CH$_3$ peak by influence of dysprosium cation (Dy$^{3+}$). This peak is verified to be a proton signal influenced by a hydroperoxide group. Peak 3 is also considered to be a proton signal influenced by a hydroperoxide group. However, it is not clearly understood as to what peak 5 is due.

Figure 2:
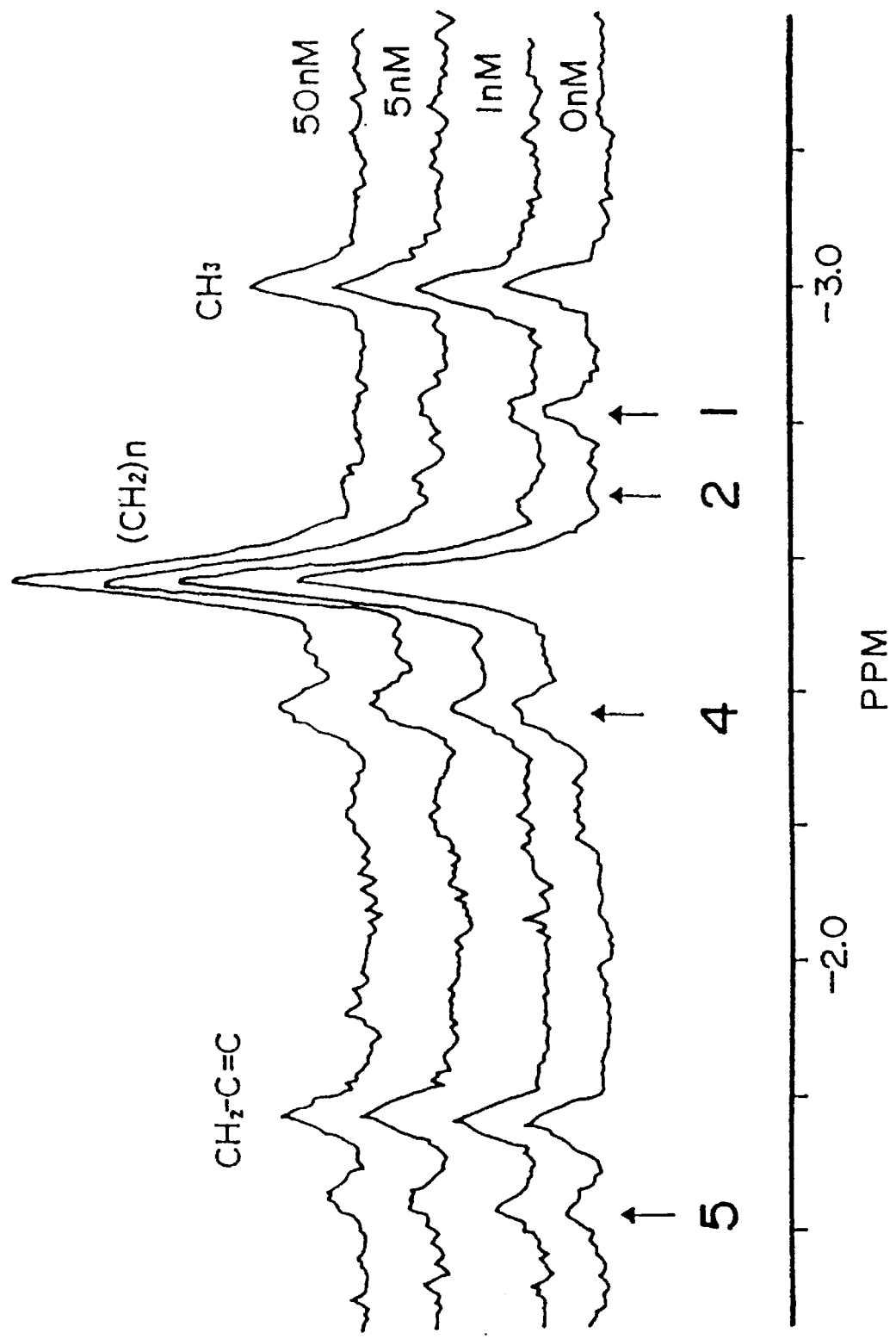
FIG. 2 is a graph showing the change in proton peaks of oxidized linoleic acid caused by addition of glutathione and glutathione peroxidase.

Change in Proton Peak of Oxidized Lipid Due to Reaction With Glutathione and Glutathione Peroxidase Next, using samples to which glutathione is added at various concentrations and glutathione peroxidase is added as a catalyst for reduction, the influence on proton peaks of oxidized lipid is observed (see FIG. 2). The values in FIG. 2 show concentrations in nM of glutathione added to the samples. In FIG. 2, it is observed that peak 1 in each of the spectra becomes lowered with higher concentration of glutathione. From this it is understood that peak 1 is a proton signal influenced by a hydroperoxide group. In contrast to peak 1, peak 2 is more distinctly observed due to the reaction with glutathione. In other words, it is considered that this peak is influenced by a hydroxide group formed by reduction of hydroperoxide group with glutathione.

Peaks 4 and 5 are not influenced by glutathione, and their derivations are not clearly understood. However, since they are observed due to oxidation of linoleic acid with lipoxygenase, they are considered to be proton signals influenced by an oxidative group such as endoperoxide.

Change With Time in Oxidation of Linoleic Acid With Soybean Lipoxygenase

Figure 3:
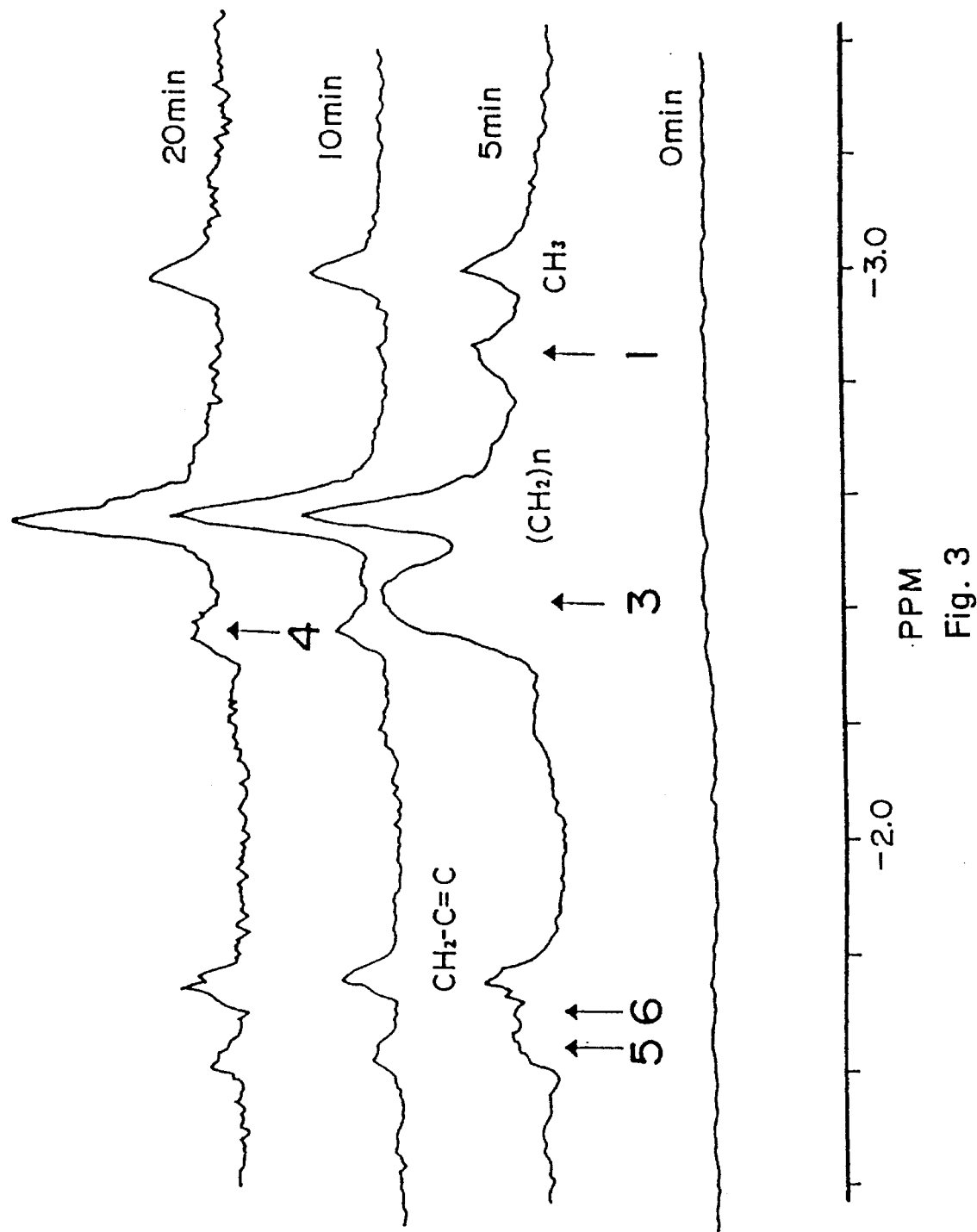
FIG. 3 is a graph showing the change with time in oxidation of linoleic acid with soybean lipoxygenase.

In the present invention, the course of oxidation of linoleic acid with soybean lipoxygenase is measured by $^1$H-NMR spectroscopy (see FIG. 3). The periods of time (min) shown in FIG. 3 indicate those for reaction with soybean lipoxygenase. Any peak is not observed in the state where linoleic acid is not oxidized with lipoxygenase, because linoleic acid is insoluble in water and hence linoleic acid is not influenced by dysprosium cation (Dy$^{3+}$). In contrast to this, linoleic acid becomes water-soluble when oxidized and oxidized lipid is influenced by dysprosium cation (Dy$^+$), so that there is observed substantial difference in proton resonance frequencies between unoxidized linoleic acid and oxidized linoleic acid.

Accordingly, when the window of the spectrum is adjusted to the proton signal of the oxidized linoleic acid, the proton signal of unoxidized linoleic acid is out of the window. Consequently, the present invention is proved to be effective as a method for detecting an oxidized lipid in a specimen.

Change With Time in Oxidation of Linoleic Acid With Soybean Lipoxygenase in the Presence of Superoxide Dismutase (SOD)

Figure 4:
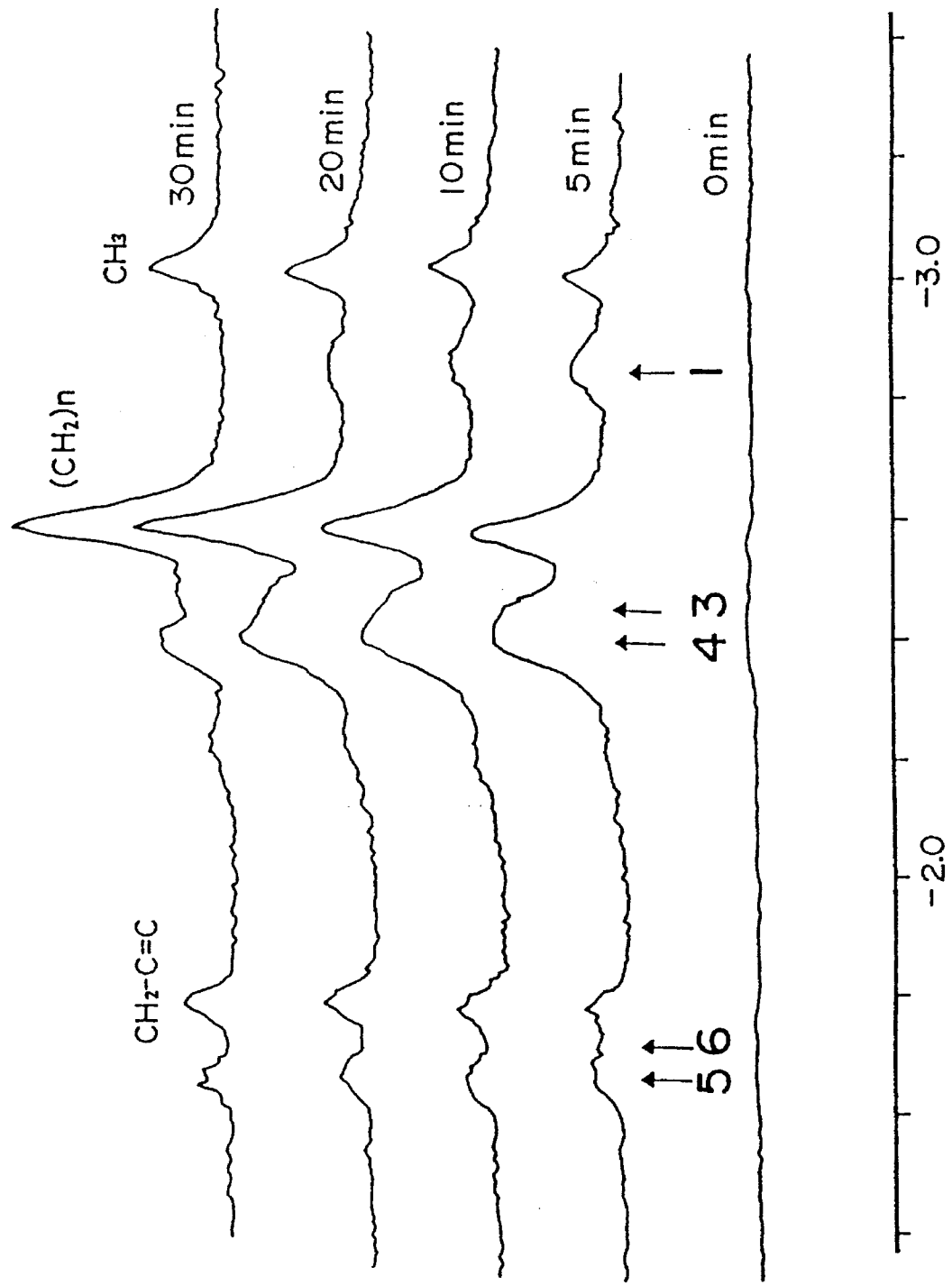
FIG. 4 is a graph showing the change with time in oxidation of linoleic acid with soybean lipoxygenase in the presence of superoxide dismutase (SOD)

Linoleic acid is oxidized with soybean lipoxygenase in the same conditions as above except that the oxidation is conducted in the presence of 0.1 U/ml superoxide dismutase (SOD). The samples are measured with time by $^1$H-NMR spectroscopy (see FIG. 4). The samples in the presence of superoxide dismutase (SOD) (see FIG. 4) show patterns distinctly different from those shown in the case in the absence of superoxide dismutase (SOD) (see FIG. 3). In other words, when superoxide dismutase (SOD) is present, peaks 1 and 3 which indicate presence of a hydroperoxide group (—OOH) in the fatty acid still appear even after 20 min from the initiation of the oxidation. These results reveal that superoxide dismutase (SOD) stabilizes the hydroperoxide group (—OOH). Heretofore, disproportionation (removal) of a superoxide has been considered to be the main activity of superoxide dismutase (SOD). From the above results, however, it is proved that superoxide dismutase (SOD) directly influences oxidized lipid, a new activity of SOD which is not related to superoxides. In other words, SOD functions to stabilize a hydroperoxide group of the already oxidized lipid and does not function to prevent the formation of an oxidized lipid.

Change With Time in Oxidation of Arachidonic Acid With Soybean Lipoxygenase

Figure 5:
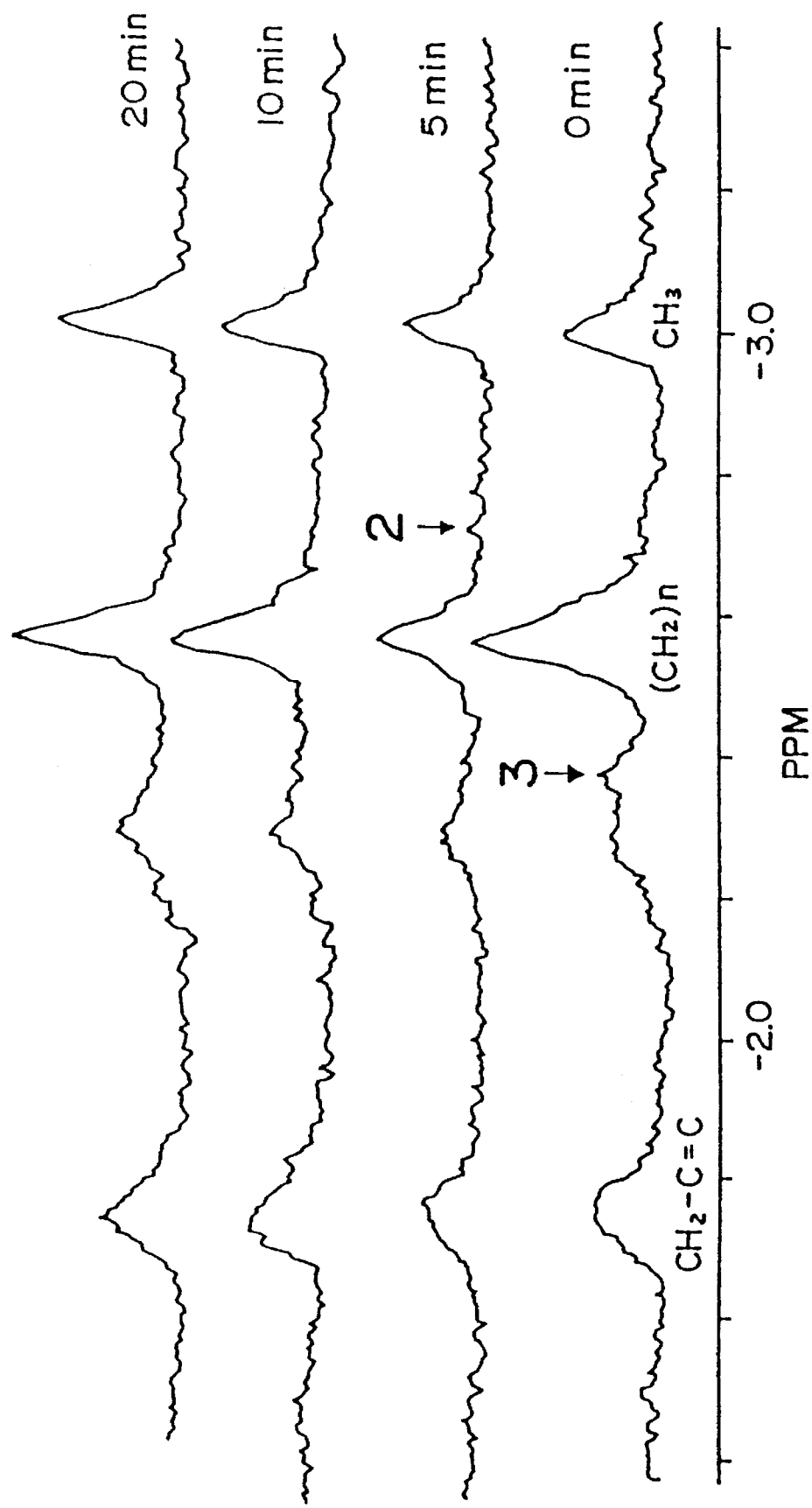
FIG. 5 is a graph showing the change with time in oxidation of arachidonic acid with soybean lipoxygenase.

Arachidonic acid is oxidized with soybean lipoxygenase in the same manner as in the oxidation of linoleic acid, and then measured by $^1$H-NMR spectroscopy (see FIG. 5). The periods of time (min) shown in FIG. 5 indicate those for reaction with soybean lipoxygenase. In contrast to the case of linoleic acid, peaks attributable to arachidonic acid have already appeared under influence of dysprosium cation (Dy$^{3+}$) before oxidation with soybean lipoxygenase. This indicates that some of arachidonic acid has already been oxidized. This is considered to be attributable to the fact that arachidonic acid has already been auto-oxidized by oxygen in air. The oxidation patterns are also different from those of linoleic acid, and there is observed no clear peak which is considered to be influenced by hydroperoxide group (—OOH).

Change With Time in Oxidation of Arachidonic Acid With Soybean Lipoxygenase in the Presence of Superoxide Dismutase (SOD)

Figure 6:
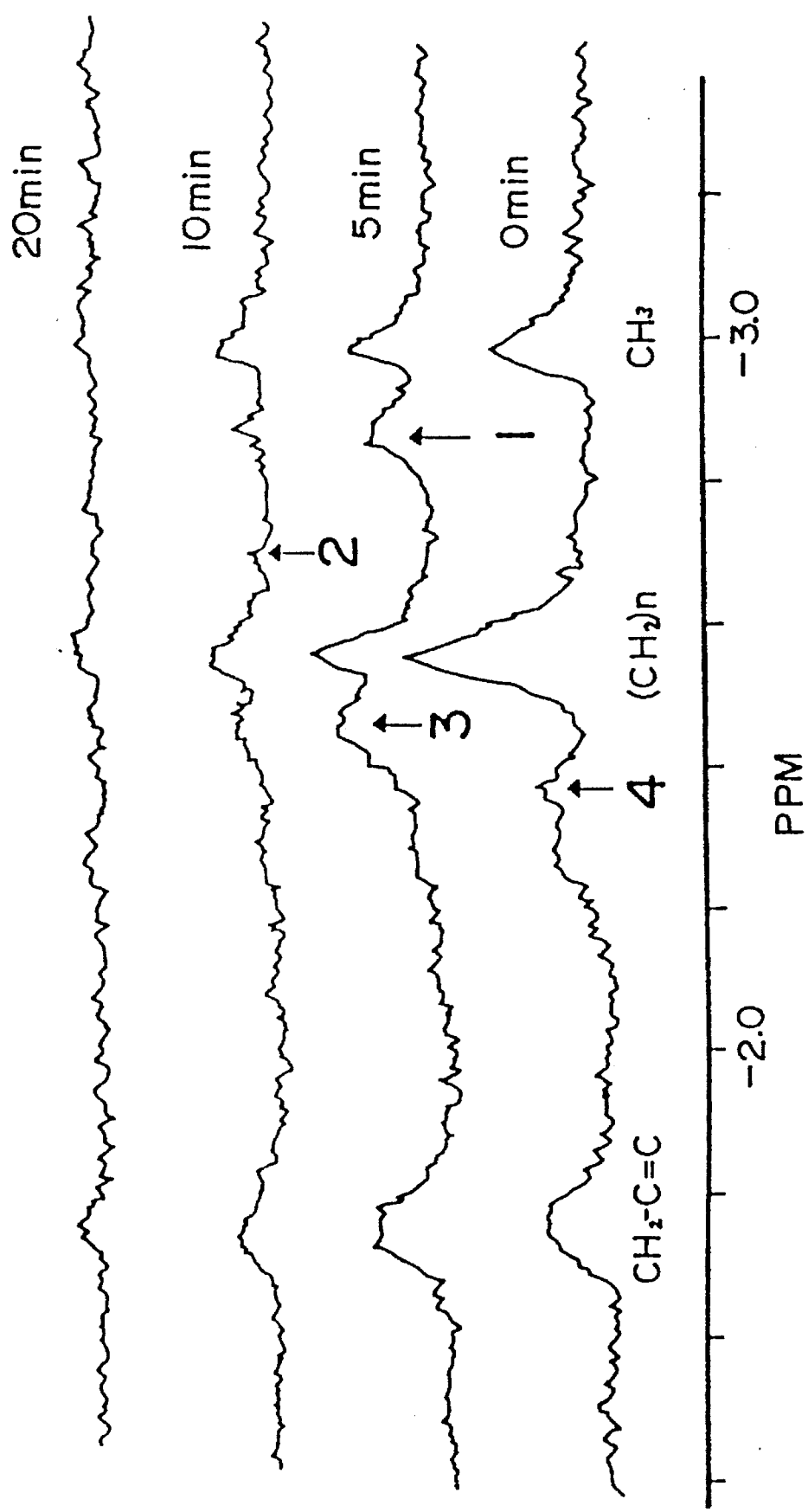
FIG. 6 is a graph showing the change with time in oxidation of arachidonic acid with soybean lipoxygenase in the presence of superoxide dismutase (SOD)

Arachidonic acid is oxidized with soybean lipoxygenase in the same conditions as above except that the oxidation is conducted in the presence of 0.1 U/ml superoxide dismutase (SOD). The samples are measured with time by $^1$H-NMR spectroscopy (see FIG. 6). Peak 1 in FIG. 6 is clearly observed at 5 min after the initiation of oxidation, as compared with the peak which is considered to be influenced by a hydroperoxide group (—OOH) in the case where superoxide dismutase (SOD) is absent. Based also on this result, it is considered that superoxide dismutase (SOD) stabilizes a hydroperoxide group (—OOH). Further, it is considered that the presence of superoxide dismutase (SOD) facilitates decomposition of $CH_2$ and $CH_3$ which constitute a skeleton of a fatty acid during oxidation step. This is proved based on the fact proton peaks ascribed to $CH_2$ and $CH_3$ substantially disappear by oxidation for a period of 15 min.

Process for Forming Oxidized Lipid

The present invention further includes a process for forming an oxidized lipid which comprises:
  adding superoxide dismutase (SOD) and $CuSO_4$ to (1) an emulsion prepared by dissolving linoleic acid or arachidonic acid in deuterated methyl alcohol and adding the solution to a deuterated phosphate buffer under stirring, or to (2) a low density lipoprotein solution sufficiently dialyzed against an undeuterated phosphate buffer; and
  irradiating the mixture with a long-wave ultraviolet light (generally, production begins within one or two minutes, reaches its maximum in two to ten minutes, then continues for twenty more minutes).

It is by virtue of the use of, for example, $Cu^{++}$ in combination with irradiation with a long-wave ultraviolet light, that water-soluble oxidized lipids having a hydroperoxide group can be obtained, especially in satisfactory amounts.

In this process, a linoleic acid emulsion or a low density lipoprotein solution is used as a lipid material.

The linoleic acid emulsion is prepared by dissolving linoleic acid in deuterated methyl alcohol at a concentration of 0.1M and adding the mixture to 20 mM deuterated phosphate buffer under stirring. Specifically, 4 mM linoleic acid emulsion is prepared.

Low density lipoprotein is separated from human plasma ky ultracentrifugation. This low density lipoprotein is sufficiently dialyzed against a 20 mM undeuterated phosphate buffer under nitrogen-saturated atmosphere. The low density lipoprotein is then adjusted with 20 mM phosphate buffer (pH 7.0) by Lowry's method to such a volume that protein concentration is 1 mg/ml.

0.1 U/ml superoxide dismutase (SOD) and 5 μM $CuSO_4$ are preliminarily added to each of lipid samples prior to irradiation of the samples with ultraviolet light.

The thus prepared lipid samples are transferred to a vessel made of borosilicate, quartz or the like. Then the samples are irradiated with long-wave ultraviolet light having the highest point of energy intensity at 365 nm for various periods of time to form oxidized lipids. This is considered to be attributable to the following fact. Unpaired electrons of $Cu^{2+}$ are excited by the long-wave ultraviolet light, and the electrons provide electrons to carbons having a double bond in the unsaturated fatty acid, thereby abstracting hydrogen atoms from the carbon atoms. Then oxidation is considered to take place in such a manner that an oxygen atom is bonded to the site where the abstraction has been occurred.

In order to form an oxidized lipid from a sample containing $Cu^{2+}$, long-wave ultraviolet rays (i.e., 315–400 nm) having the highest point of energy intensity about 365 nm are optimum. Generally, a wavelength range of about 320 to about 400 nm may be utilized, though it may be possible to utilize visible light above 400 nm, such as fluorescent light, with increased wattage. Wavelengths of equal to less than 300 nm cannot be used because that would decompose the polyunsaturated acid structure. With irradiation of such a sample with short-wave ultraviolet rays having the highest point of energy intensity around 254 nm, it is impossible to form a peroxide lipid containing a hydroperoxide group.

Further, it is also possible to produce an oxidized lipid containing a hydroperoxide group by irradiation with $Fe^{3+}$ or the like (e.g., Fe cation such as $FeSO_4$) with long range ultraviolet light. Moreover, oxidation of arachidonic acid in the above-mentioned method also enables a water-soluble oxidized lipid containing a hydroperoxide group, which is believed to have considerable influence on a living body, to be produced.

Method for Forming Dysprosium Tripolyphosphate

The thus formed oxidized lipid is added with a dysprosium tripolyphosphate as a lanthanide shift reagent.

200 mM dysprosium chloride ($DyCl_3$) and 480 mM pentasodium tripolyphosphate are thoroughly stirred in deuterium oxide. The solution, though it has a sediment, is adjusted to pH 7.4 with deuterium chloride, thereby some of the sediment will be dissolved. Then the solution is centrifuged at 3000 g for 30 min to remove the remaining sediment. This dysprosium tripolyphosphate anion ($Dy(ppp)_2^{-7}$) solution is rapidly added to the oxidized samples at a concentration of 40 mM.

Determination of Oxidized Lipid by $^1$H-NMR Spectroscopy

For the spectroscopy, hydrogen nucleus (proton) NMR analysis ($^1$H-NMR spectroscopy) by means of a nuclear magnetic resonance spectrometer (Bruker AM360 series) is used.

NMR is conducted using a nuclear magnetic resonance spectrometer of 360MHz. Proton spectra are obtained in quadrature detection mode at a probe temperature of 308° K. The spectra are accumulated by repeating Free Induction Decay 512 times for linoleic acid samples and 32 times for low density lipoprotein samples. HDO and $H_2O$ proton signals are presaturated by 4 sec of 200 mW of gated, continuous-wave, single-frequency irradiation. A spectral width of 7246 Hz and acquisition time of 0.565 sec are selected.

Results of Determination

Oxidation patterns of linoleic acid using $Cu^{2+}$ and irradiation with ultraviolet light are very similar to those using soybean lipoxygenase with respect to proton NMR spectra.

Figure 7:
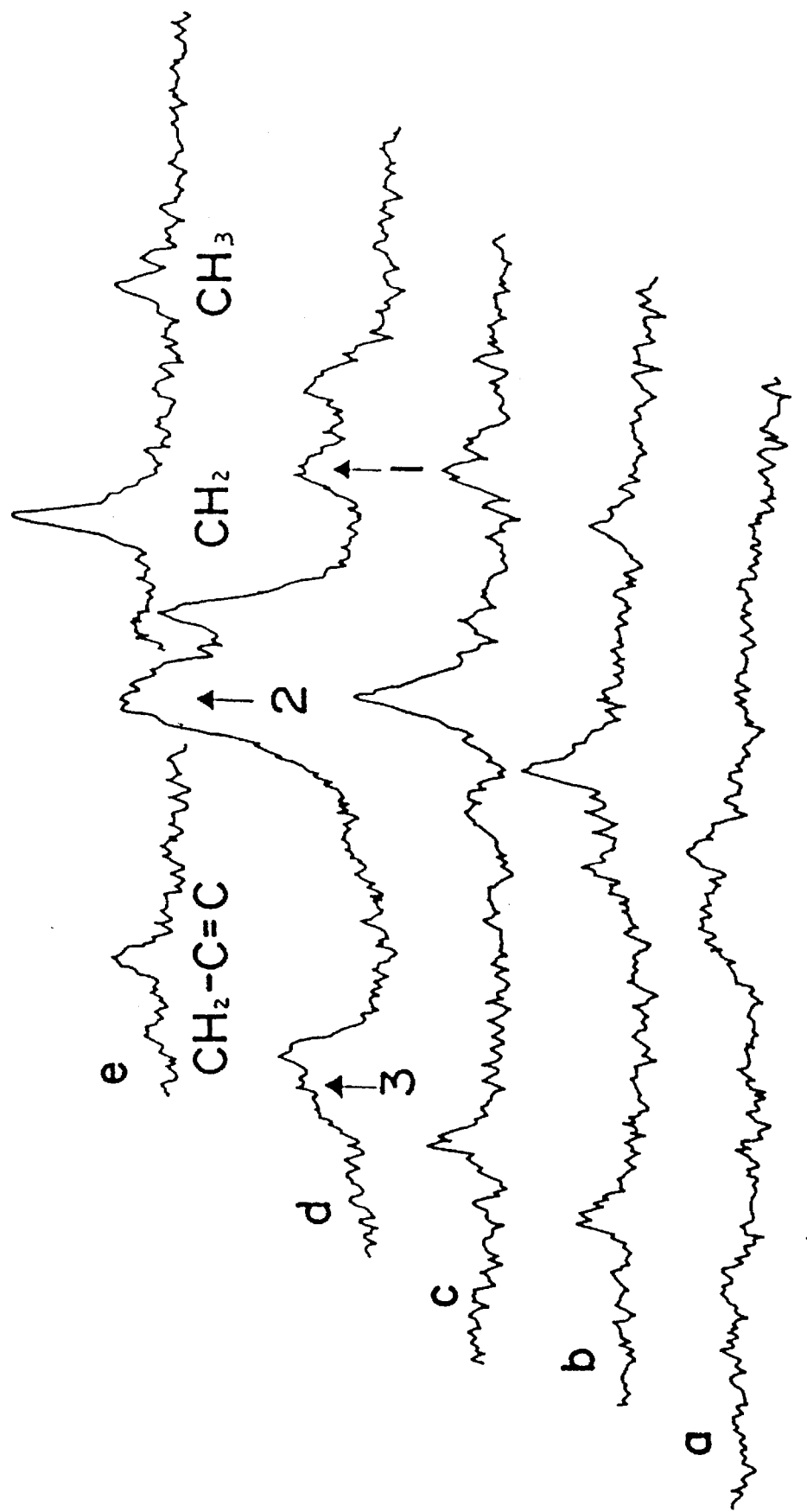
FIG. 7 is a graph showing the results of measurement with time of oxidized samples by means of a proton nuclear magnetic resonance spectrometer, the oxidized samples having been prepared by preliminarily adding superoxide dismutase (SOD) and 5 µM $CuSO_4$ to the linoleic acid samples, followed by irradiation with long-wave ultraviolet light.

FIG. 7 shows results of measurement with time of oxidized samples by means of a proton nuclear magnetic resonance spectrometer, the oxidized samples having been prepared by preliminarily adding superoxide dismutase (SOD) and 5 μM $CuSO_4$ to the linoleic acid samples already prepared in the above-mentioned manner, followed by irradiation with long-wave ultraviolet light. Pattern b in FIG. 7 is spectrum of the sample subjected to irradiation with long-wave ultraviolet light for 5 min. Patterns c, d, and e are spectra of the samples subjected to irradiation with long-wave ultraviolet light for 10, 20, and 30 min respectively. Incidentally, pattern a is spectrum of the sample subjected to no irradiation with long-wave ultraviolet light.

Peak 1 in FIG. 7 is apparently understood to be a proton signal influenced by a hydroperoxide group (—OOH). Peaks 2 and 3 are considered to be proton signals each influenced by a hydroperoxide group (—OOH) and another oxidative group (however, it has not yet been confirmed what oxygenated groups they are).

Figure 8:
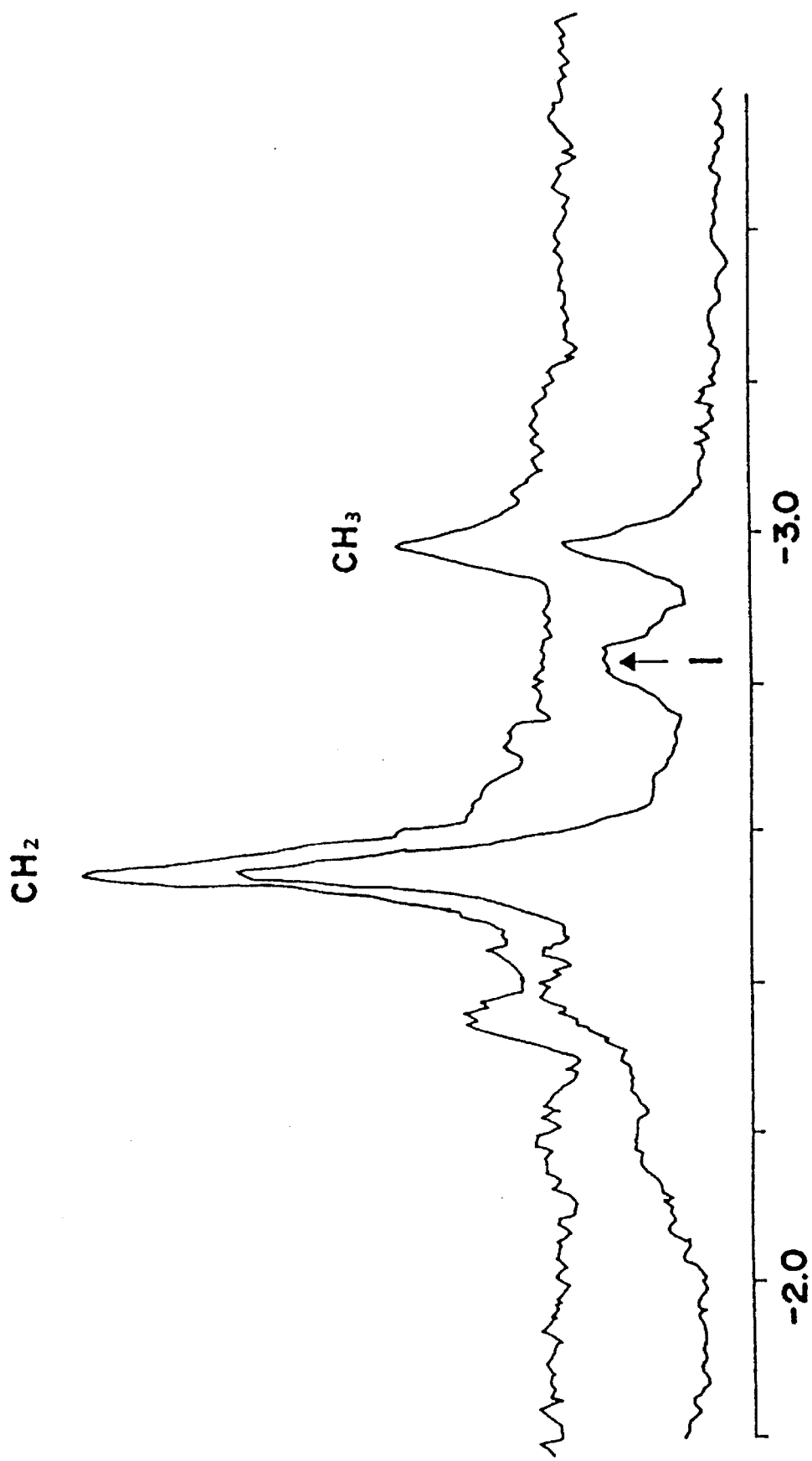
FIG. 8 is a graph showing the results of measurement with time by means of a proton nuclear magnetic spectrometer with respect to linoleic acid samples oxidized by irradiation with long-wave ultraviolet light.

FIG. 8 shows the results of measurement with time by means of a proton nuclear magnetic spectrometer with respect to the linoleic acid samples oxidized by irradiation with long-wave ultraviolet light. The lower spectrum is derived from an oxidized lipid sample to which nothing has been added and which has been allowed to react for 10 min prior to the measurement. The upper spectrum is derived from an oxidized lipid sample to which 50 nM glutathione and 0.2 U/ml (final concentration) glutathione peroxidase have been added and which has been allowed to react for 10 min prior to the measurement.

In the upper spectrum, peak 1 disappears under the influence of glutathione. From this, peak 1 is confirmed to be a proton peak influenced by a hydroperoxide group. This is based on the ground that glutathione peroxidase has been proved to convert its hydroperoxide group to a hydroxide group in the presence of glutathione.

It may be considered that the linoleic acid in the samples is a water-soluble linoleic acid containing both a hydroperoxide group having considerable influence on a living body and a polar oxidative group such as an epoxy group and an endoperoxy group. The reason is that an oxidized lipid containing only a hydroperoxide group is hardly water-soluble but is rather soluble in an organic solvent such as ethyl ether. However, with respect to oxidized linoleic acid, it might be water-soluble even if it contains only a hydroperoxide group. The hydroperoxide group can be stabilized by the presence of superoxide dismutase (SOD).

Figure 9:
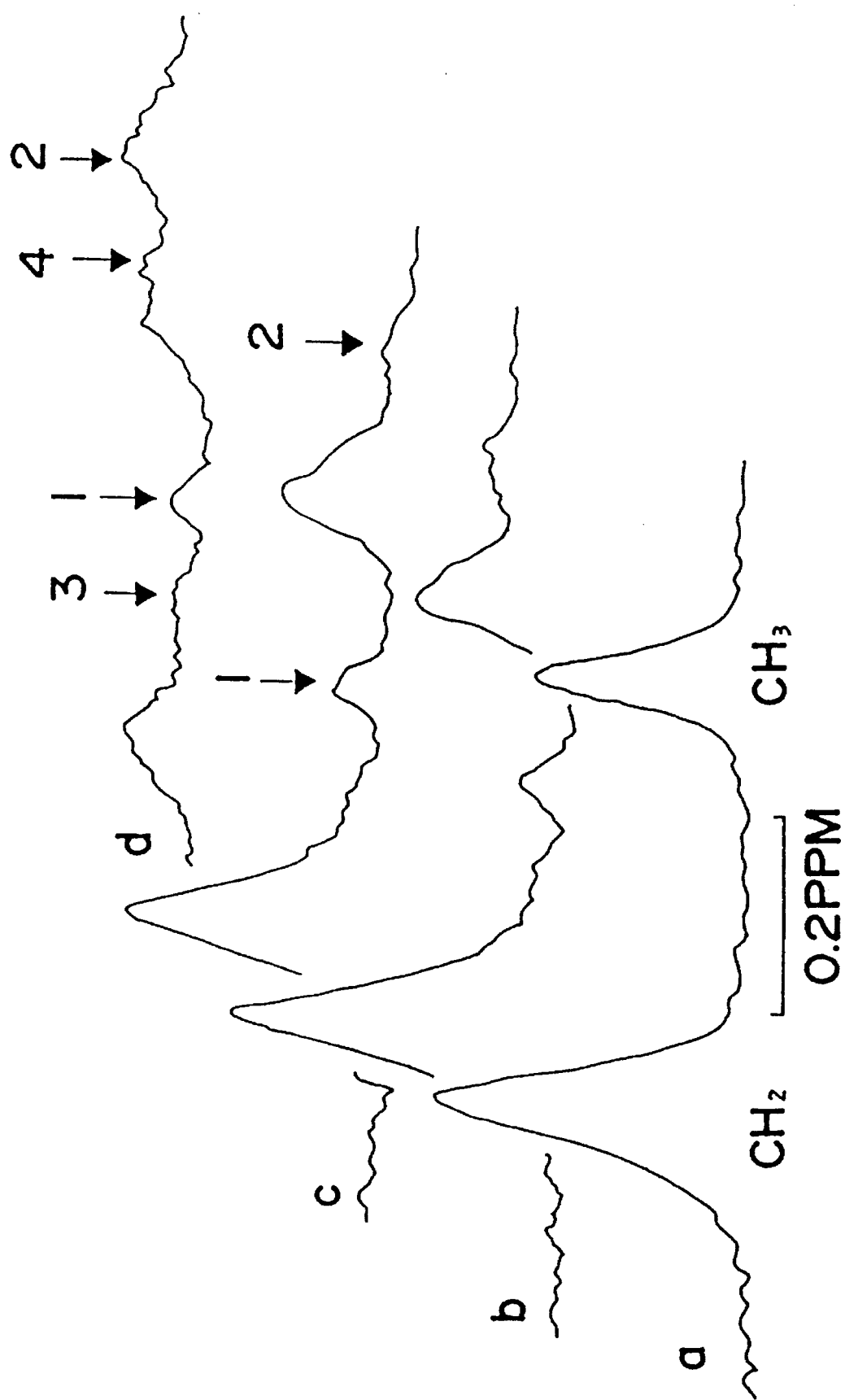
FIG. 9 is a graph showing the results of measurement of samples in such a procedure that superoxide dismutase (SOD) and 5 µM $CuSO_4$ are added to a low density lipoprotein solution, then the mixture is irradiated with long-wave ultraviolet light to oxidize the low density lipoprotein, and a dysprosium tripolyphosphate solution is added thereto, followed by measurement of the resultant samples by means of a proton nuclear magnetic resonance spectrometer.

Formation of Oxidized Low Density Lipoprotein by the Use of $Cu^{2+}$ and Irradiation with UV:

FIG. 9 shows results of measurement of samples in the following procedure: superoxide dismutase (SOD) and 5 μM $CuSO_4$ are added to a low density lipoprotein solution, then the mixture is irradiated with long-wave ultraviolet light to oxidize the low density lipoprotein, and a dysprosium tripolyphosphate anion solution is added thereto, followed by measurement of the resultant samples by means of a proton nuclear magnetic resonance spectrometer. Pattern b in FIG. 9 is derived from the sample irradiated with long-wave ultraviolet light for 30 min. Patterns c and d are derived from the samples irradiated with long-wave ultraviolet light for 60 min and 90 min, respectively. Incidentally, pattern a is derived from the sample subjected to no irradiation with long-wave ultraviolet light.

$CH_2$ and $CH_3$ in this Figure indicate proton signals corresponding to $CH_2$ and $CH_3$ in the skeleton of the fatty acid in the low density lipoprotein solution, respectively.

Peak 1 and peak 2 are separated from the peaks attributable to $CH_2$ and $CH_3$ due to the addition of the shift reagent, respectively. These peaks 1 and 2 are proton signals influenced by a cholesterol hydroperoxide group esterified with the fatty acid. The reason is that, of lipids present in the low density lipoprotein solution, no lipid other than cholesterol ester-bonded to the fatty acid can occupy the great peak as shown in the Figure in view of the quantity.

In other words, when these peaks are observed, it is recognized that a cholesterol hydroperoxide group is present in samples.

Stabilization of Hydroperoxide Group in Lipid by Acidification of Solution or by Addition of Ethylenediaminetetraacetic Acid (EDTA)

Figure 10:
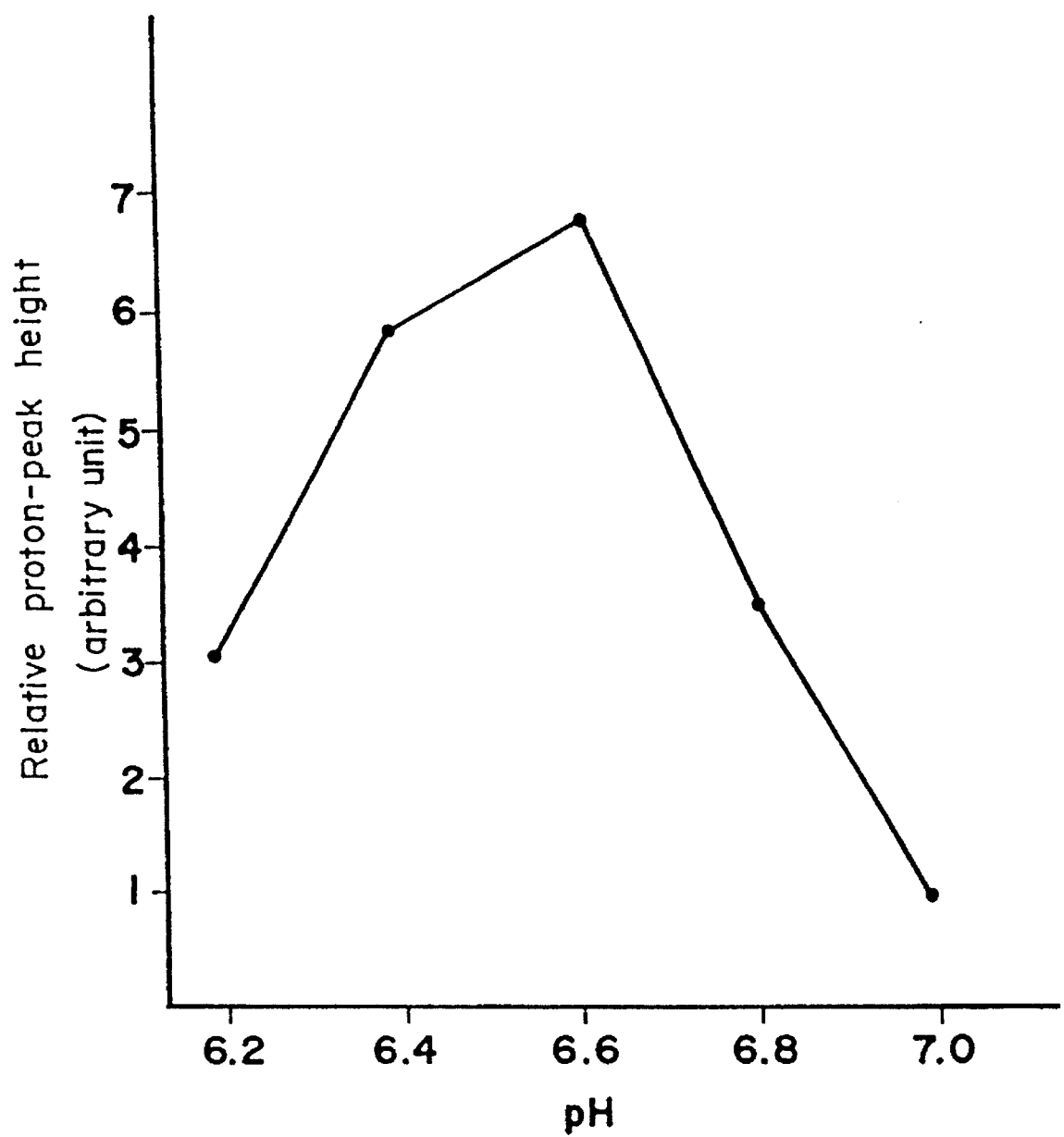
FIG. 10 is a graph showing the results of rough quantitative determination by measuring the heights of peak 1 influenced by a hydroperoxide group in low density lipoprotein.

FIG. 10 is a trace showing the results of rough quantitative determination by measuring the heights of peak 1 influenced by a hydroperoxide group in low density lipoprotein. The quantity of hydroperoxide cholesterol in the low density lipoprotein reaches the peak at pH 6.6. It is considered that a hydroperoxide group is stabilized even under acidities lower than pH 6.6. Since a protein in the form of a lipoprotein such as a low density lipoprotein undergoes degeneration under acidity of pH 6 or lower, the quantity of the hydroperoxide group is apparently measured such that it becomes lowered under acidity of pH 6 or lower. When linoleic acid is used, a hydroperoxide group in linoleic acid is stabilized even under strong acidity of pH 3 to pH 4. On the other hand, addition of a chelating agent such as EDTA is proved to be capable of stabilizing the above-mentioned hydroperoxide group even under neutrality in the vicinity of pH 7.0. These phenomena indicate that acidification of an oxidized lipid or addition of a chelating agent enables the oxidized lipid samples prepared in the manner as described above to be preserved.

As described above, a hydroperoxide group of fatty acids in LDL is stabilized at pH 6.6. If it is more acidic, proton peaks, indicating the existence of a hydroperoxide group, become lower. This is because denaturation of protein in LDL occurs, not because a hydroperoxide group is destroyed. This is clear from the fact that linoleic acid without protein is stabilized in a strong acid condition at pH 4.0. For this reason, it can be said that the stability of a hydroperoxide group of oxidized free fatty acid is increased if the acidity is weaker than pH 6.6 in the phosphate deuteride buffer. A small amount of a hydroperoxide group can exist in a neutral phosphate deuteride buffer (without adding EDTA or some similar chelating agent) for a few minutes to several hours. It is better to avoid chelating agents as much as possible in creating a strong acid condition when the method is applied to pharmaceuticals; EDTA is the most frequently used chelating agent as an anticoagulant in the medical and biochemical fields and is not harmful to humans if the amount used is small, nonetheless it is best not to use it at all.

Figure 11:
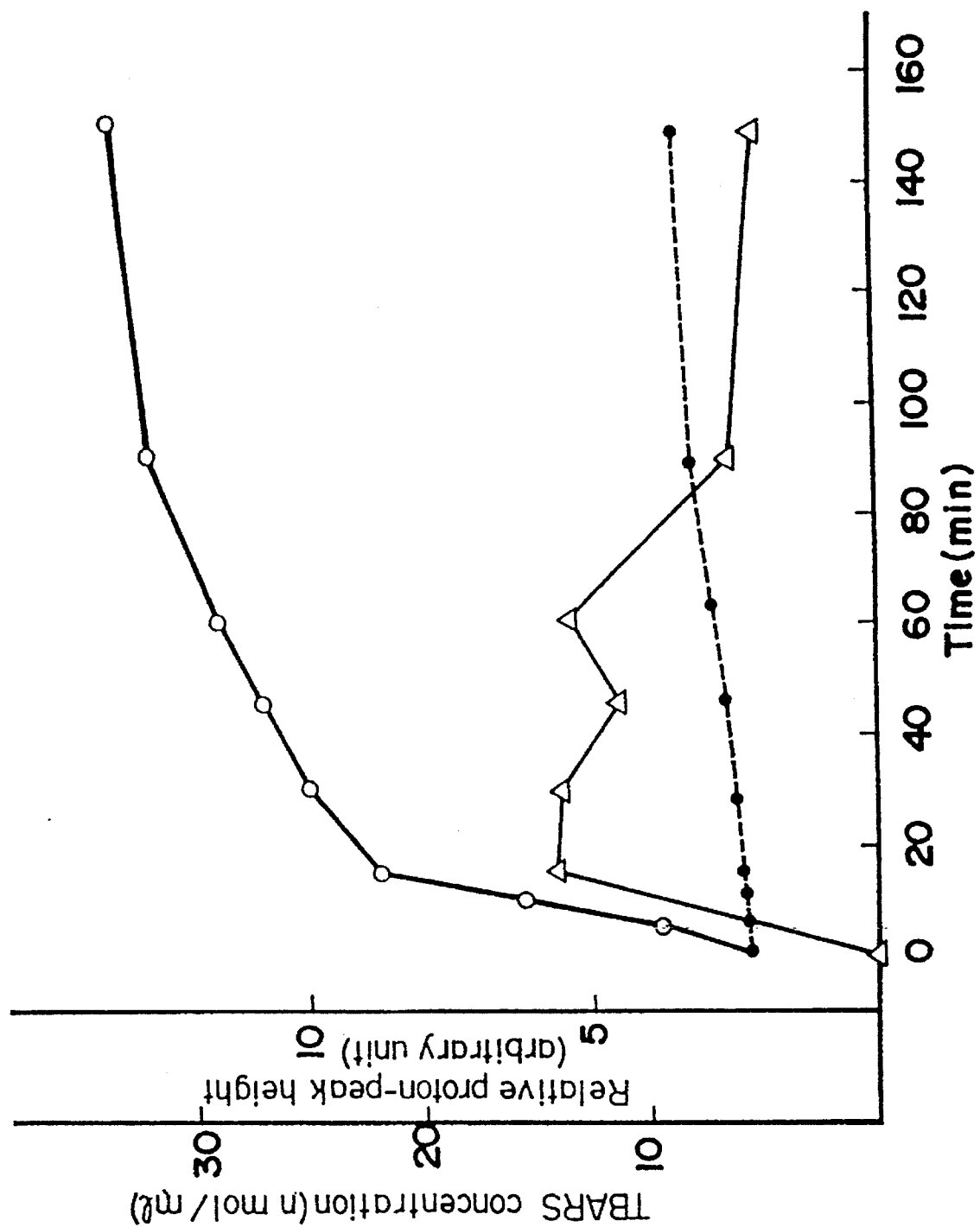
FIG. 11 is a graph showing the results of measurements of change with time of oxidation of the low density lipoprotein irradiated with long-wave ultraviolet light by thiobarbituric acid reaction substance measuring method and by $^1$H-NMR spectroscopy.

Comparison Between Thiobarbituric Acid Reaction Substance Measuring Method and $^1$H-NMR Spectroscopy by the Use of Oxidized Low Density Lipoprotein FIG. 11 shows the results of measurements of change with time of oxidation of the low density lipoprotein irradiated with long-wave ultraviolet light by thiobarbituric acid reactive substance measuring method which is conventionally widely employed (white circles in FIG. 11) and by $^1$H-NMR spectroscopy (white triangles in FIG. 11). Incidentally, a sample is taken as a control in advance of the irradiation with long-wave ultraviolet light, and allowed to stand in a dark place. Change of oxidation of the low density lipoprotein with respect to the control sample is also measured with time by TBARS measuring method, the results are shown by black circles in FIG. 11.

In thiobarbituric acid reactive substance measuring method, a thiobarbituric acid reactive substance which reflects accumulative oxidation degree rapidly increases from immediately after the irradiation with long-wave ultraviolet light, and the increase rate thereof becomes moderate 30 min later. The height of peak 1 reaches the highest value 20 min after the initiation of the irradiation. Thereafter, however, the height of peak 1 becomes lower, although the value for the thiobarbituric acid reactive substance continues to increase even after elapse of time of 60 min. There is observed disparity between them. The thiobarbituric acid reactive substance is measured in terms of the products decomposed through oxidation of a lipid, such as methyl malonaldehyde. Accordingly, the value represents the accumulation of the products.

On the other hand, in the $^1$H-NMR spectroscopy method according to the present invention, the water-soluble oxidized lipid having a hydroperoxide group per se is measured. Accordingly, as disappearance of the unstable hydroperoxide group occurs, the height of the peak 1 decreases directly reflecting the disappearance of the hydroperoxide group.

As described above, although the conventional thiobarbituric acid reaction substance measuring method can detect occurrence of oxidation of a lipid, the method is not capable of proving the existence of a certain kind of an oxidized lipid in a sample.

The present invention detects and determines a specimen to include a water-soluble oxidized lipid through analyzing the difference in proton signals by spectroscopy which is observed, when dysprosium tripolyphosphte anion $(Dy(ppp)_2^{-7})$ is added to the specimen, between the case where the sample contains a water-soluble oxidized lipid and the case where the sample does not contain a water-soluble oxidized lipid. Therefore, a specimen is readily and accurately determined to contain a water-soluble oxidized lipid.

In other words, according to the present invention, a specimen can directly be detected and determined to contain a water-soluble oxidized lipid through analyzing the difference in proton signals by spectroscopy.

Furthermore, even if an impurity is contained in a specimen, the specimen can be detected and determined to contain an oxidized lipid without influence of the presence of the impurity.

Moreover, the determination process is extremely simple by virtue of the adoption of the spectroscopic proton signal analysis of the specimen, and the specimen can be detected and determined to contain an oxidized lipid in a short period of time. In addition, since no treatment of the specimen such as esterification is required at all, there is no longer any undesired possibility of denaturation of the specimen.

On the other hand, by addition of a lanthanide shift reagent such as dysprosium cation ($Dy^{3+}$) to an oxidized lipid and subsequent $^1$H-NMR spectroscopic analysis, it has for the first time been rendered possible to confirm the presence of the hydroxide group (—OH) in the oxidized lipid.

Furthermore, it is successfully attained by the present invention to form a water-soluble oxidized lipid containing an unstable hydroperoxide group, which is considered to have marked influence on a living body.

In addition, there is found cumulative advantageous effect attendant upon the formation of the water-soluble oxidized lipid having a hydroperoxide group by the use of $Cu^{2+}$ and irradiation with ultraviolet light, and on the basis of the finding, it is successfully accomplished to detect and determine the water-soluble oxidized lipid containing a hydroperoxide group by $^1$H-NMR spectroscopic analysis.

Still further, it is rendered possible to detect presence of an oxidized cholesterol-fatty acid ester contained in low density lipoprotein at a concentration substantially the same as or lower than that in human plasma.

From the above effects, the proton-NMR spectroscopic analysis by means of a nuclear magnetic resonance spectrometer is considered to be effective as a process which is capable of directly detecting the presence of an oxidized lipid in a biomaterial containing many impurities such as plasma.

The method of detecting a water soluble oxidized lipid may be used to evaluate the degree of oxidation of a lipid (e.g., low density lipoprotein or other lipoproteins) from a mammalian body (e.g., tissue or body fluids) or a lipid used in a food or other industrial product. For instance, the degree of oxidation of edible oil is related to the deterioration of the oil. Furthermore, the quality of motor oil (and other various types of oil used in industrial products) is determined by the degree of oxidation or susceptibility to oxidation. Thus, the method of detecting oxidized lipid would be useful in testing product quality.

Further variations and modifications of the foregoing will be apparent to those skilled in the art and such variations and modifications are attended to be encompassed by the claims that are appended hereto.

Japanese Priority Application 4-200082, filed on Jun. 18, 1992, and Japanese Priority Application 5-144170, filed on May 12, 1993, are relied on and incorporated by reference in their entirety.

What is claimed:

1. A process for detecting the presence of a water-soluble oxidized lipid in a specimen, said process comprising adding a lanthanide shift reagent to a specimen and subjecting the resultant mixture to spectroscopy to detect the presence of said water-soluble oxidized lipid, wherein said water-soluble oxidized lipid is a water-soluble oxidized lipid having a hydroperoxide group.

2. The process according to claim 1, wherein the lanthanide shift reagent is dysprosium, europium or thulium cation.

3. The process according to claim 1, wherein the lanthanide shift reagent is dysprosium, europium or thulium tripolyphosphate anion.

4. The process according to claim 1, further comprising stabilizing said water-soluble oxidized lipid by maintaining said water-soluble oxidized lipid under strong acidic conditions or adding to said water-soluble oxidized lipid a chelating agent selected from the group consisting of dysprosium tripolyphosphate, ethylenediaminetetraacetic acid (EDTA) and superoxide dismutase (SOD).

5. The process according to claim 1, wherein said spectroscopy is $^{13}$C-NMR spectroscopy or $^1$H-NMR spectroscopy.

6. The process according to claim 1, said process consisting essentially of adding a lanthanide shift reagent to a specimen and subjecting the resultant mixture to spectroscopy to detect the presence of said water-soluble oxidized lipid, wherein said water-soluble oxidized lipid is a water-soluble oxidized lipid having a hydroperoxide group; optionally stabilizing said water-soluble oxidized lipid by maintaining said water-soluble oxidized lipid under strong acidic conditions or adding to said water-soluble oxidized lipid a chelating agent selected from the group consisting of dysprosium tripolyphosphate, ethylenediaminetetraacetic acid (EDTA) and superoxide dismutase (SOD).

7. A process for forming a water-soluble oxidized lipid, said process comprising:

adding superoxide dismutase (SOD) and Cu or Fe cation to (i) an emulsion prepared by dissolving linoleic acid or arachidonic acid in deuterated methyl alcohol and adding the solution to a deuterated phosphate buffer under stirring, or to (ii) a low density lipoprotein solution sufficiently dialyzed against an undeuterated phosphate buffer; and irradiating the mixture with a long-wave ultraviolet light to form said water-soluble oxidized lipid, wherein said water-soluble oxidized lipid is a water-soluble oxidized lipid having a hydroperoxide group.

8. The process according to claim 7, wherein said Cu cation is $CuSO_4$ and said Fe cation is $FeSO_4$.

9. A water-soluble oxidized lipid prepared by the process according to claim 7.

10. The process according to claim 7, said process consisting essentially of:

adding superoxide dismutase (SOD) and Cu or Fe cation to (i) an emulsion prepared by dissolving linoleic acid or arachidonic acid in deuterated methyl alcohol and adding the solution to a deuterated phosphate buffer under stirring, or to (ii) a low density lipoprotein solution sufficiently dialyzed against an undeuterated phosphate buffer; and irradiating the mixture with a long-wave ultraviolet light to form said water-soluble oxidized lipid, wherein said water-soluble oxidized lipid is a water-soluble oxidized lipid having a hydroperoxide group;

optionally stabilizing said water-soluble oxidized lipid by maintaining said water-soluble oxidized lipid under strong acidic conditions or adding to said water-soluble oxidized lipid a chelating agent selected from the group consisting of dysprosium tripolyphosphate, ethylenediaminetetraacetic acid (EDTA) and superoxide dismutase (SOD).

11. The process according to claim 7, wherein said long-wave ultraviolet light has a wavelength range of about 320 to about 400 nm.

12. The process according to claim 7, wherein said water-soluble oxidized formed by said process are in the form of free fatty acids.

13. The process according to claim 7, further comprising stabilizing said water-soluble oxidized lipid by maintaining said water-soluble oxidized lipid under strong acidic conditions or adding to said water-soluble oxidized lipid a chelating agent selected from the group consisting of dysprosium tripolyphosphate, ethylenediaminetetraacetic acid (EDTA) and superoxide dismutase (SOD).

14. A process for detecting a water-soluble oxidized lipid, said process comprising:

adding superoxide dismutase (SOD) and Cu or Fe cation to (i) an emulsion prepared by dissolving linoleic acid or arachidonic acid in deuterated methyl alcohol to form a solution and adding the solution to a deuterated phosphate buffer under stirring, or to (ii) a low density lipoprotein solution sufficiently dialyzed against an undeuterated phosphate buffer, to form a mixture, irradiating the mixture with a long-wave ultraviolet light to form a water-soluble oxidized lipid, and adding a dysprosium tripolyphosphate anion to the water-soluble oxidized lipid, and detecting said water-soluble oxidized lipid by proton-NMR spectroscopy by means of a nuclear magnetic resonance spectrometer, wherein said water-soluble oxidized lipid is a water-soluble oxidized lipid having a hydroperoxide group.

15. The process according to claim 14, further comprising stabilizing said water-soluble oxidized lipid by maintaining said water-soluble oxidized lipid under strong acidic conditions or adding to said water-soluble oxidized lipid a chelating agent selected from the group consisting of dysprosium tripolyphosphate, ethylenediaminetetraacetic acid (EDTA) and superoxide dismutase (SOD).

16. The process according to claim 14, wherein said spectroscopy is $^{13}C$-NMR spectroscopy or $^1H$-NMR spectroscopy.

17. The process according to claim 14, wherein said Cu cation is $CuSO_4$ and said Fe cation is $FeSO_4$.

18. The process according to claim 14, said process consisting essentially of:

adding superoxide dismutase (SOD) and Cu or Fe cation to (i) an emulsion prepared by dissolving linoleic acid or arachidonic acid in deuterated methyl alcohol to form a solution and adding the solution to a deuterated phosphate buffer under stirring, or to (ii) a low density lipoprotein solution sufficiently dialyzed against an undeuterated phosphate buffer, to form a mixture, irradiating the mixture with a long-wave ultraviolet light to form a water-soluble oxidized lipid, and adding a dysprosium tripolyphosphate anion to the water-soluble oxidized lipid, and detecting said water-soluble oxidized lipid by proton-NMR spectroscopy by means of a nuclear magnetic resonance spectrometer, wherein said water-soluble oxidized lipid is a water-soluble oxidized lipid having a hydroperoxide group;

optionally stabilizing said water-soluble oxidized lipid by maintaining said water-soluble oxidized lipid under strong acidic conditions or adding to said water-soluble oxidized lipid a chelating agent selected from the group consisting of dysprosium tripolyphosphate, ethylenediaminetetraacetic acid (EDTA) and superoxide dismutase (SOD).

19. The process according to claim 14, wherein said long-wave ultraviolet light has a wavelength range of about 320 to about 400 nm.

20. A process for forming a water-soluble oxidized lipid, said process comprising:

adding superoxide dismutase (SOD) and Cu or Fe cation to (i) an emulsion prepared by dissolving linoleic acid or arachidonic in methyl alcohol to form a solution and adding the solution to a phosphate buffer under stirring, or to (ii) a low density lipoprotein solution sufficiently dialyzed against an undeuterated phosphate buffer, to form a mixture; and irradiating the mixture with a long-wave ultraviolet light to form said water-soluble oxidized lipid, wherein said water-soluble oxidized lipid is a water-soluble oxidized lipid having a hydroperoxide group.

21. The process according to claim 20, wherein said Cu cation is $CuSO_4$ and said Fe cation is $FeSO_4$.

22. The process according to claim 20, said process consisting essentially of:

adding superoxide dismutase (SOD) and Cu or Fe cation to (i) an emulsion prepared by dissolving linoleic acid or arachidonic in methyl alcohol to form a solution and adding the solution to a phosphate buffer under stirring, or to (ii) a low density lipoprotein solution sufficiently dialyzed against an undeuterated phosphate buffer, to form a mixture; and irradiating the mixture with a long-wave ultraviolet light to form said water-soluble oxidized lipid, wherein said water-soluble oxidized lipid is a water-soluble oxidized lipid having a hydroperoxide group;

optionally stabilizing said water-soluble oxidized lipid by maintaining said water-soluble oxidized lipid under strong acidic conditions or adding to said water-soluble oxidized lipid a chelating agent selected from the group consisting of dysprosium tripolyphosphate, ethylenediaminetetraacetic acid (EDTA) and superoxide dismutase (SOD).

23. The process according to claim 20, wherein said long-wave ultraviolet light has a wavelength range of about 320 to about 400 nm.

24. The process according to claim 20, wherein said water-soluble oxidized formed by said process are in the form of free fatty acids.

25. The process according to claim 20, further comprising stabilizing said water-soluble oxidized lipid by maintaining said water-soluble oxidized lipid under strong acidic conditions or adding to said water-soluble oxidized lipid a chelating agent selected from the group consisting of dysprosium tripolyphosphate, ethylenediaminetetraacetic acid (EDTA) and superoxide dismutase (SOD).

* * * * *